United States Patent
Marash

(10) Patent No.: US 9,474,913 B2
(45) Date of Patent: Oct. 25, 2016

(54) UNIVERSAL TELETHERAPY TREATMENT ROOM ARRANGEMENT

(75) Inventor: Michael Marash, Rishon Le'tzion (IL)

(73) Assignee: P-CURE, LTD., Lod (IL)

( * ) Notice: Subject to any disclaimer, the term of this patent is extended or adjusted under 35 U.S.C. 154(b) by 445 days.

(21) Appl. No.: 14/114,210

(22) PCT Filed: Apr. 29, 2012

(86) PCT No.: PCT/IL2012/050149
§ 371 (c)(1),
(2), (4) Date: Oct. 27, 2013

(87) PCT Pub. No.: WO2012/150594
PCT Pub. Date: Nov. 8, 2012

(65) Prior Publication Data
US 2014/0056403 A1    Feb. 27, 2014

Related U.S. Application Data

(60) Provisional application No. 61/481,205, filed on May 1, 2011.

(51) Int. Cl.
*A61B 6/03*     (2006.01)
*A61N 5/10*    (2006.01)
(Continued)

(52) U.S. Cl.
CPC ............ *A61N 5/103* (2013.01); *A61B 6/03* (2013.01); *A61B 6/032* (2013.01); *A61B 6/04* (2013.01); *A61B 6/0492* (2013.01);
(Continued)

(58) Field of Classification Search
CPC ............. A61N 5/1049; A61N 5/103; A61N 2005/1061
See application file for complete search history.

(56) References Cited

U.S. PATENT DOCUMENTS 5,851,182 A    12/1998    Sahadevan
7,796,730 B2    9/2010    Marash et al.
(Continued)

FOREIGN PATENT DOCUMENTS

CN    101574266 A    11/2009
CN    101889870 A    11/2010

OTHER PUBLICATIONS

Office Action from the State Intellectual Property Office of the People's Republic of China, Dated Sep. 6, 2015 for parallel China patent application 201280032417.5.
(Continued)

*Primary Examiner* — Hoon Song
(74) *Attorney, Agent, or Firm* — Simon Kahn; Chanoch Kahn

(57) ABSTRACT

A teletherapy treatment arrangement constituted of: a control unit; a 3 dimensional imager having an effective patient plane; at least one 2 dimensional imager arranged to provide a pair of 2 dimensional images along planes generally orthogonal to the effective patient plane of the 3 dimensional imager; and a patient positioner arranged to secure a target tissue in a fixed relationship to the patient positioner, the control unit arranged to: input a planned treatment position of the patient target tissue; in the event that the planned treatment position is consonant with the effective patient plane of the 3 dimensional imager, obtain position information of the target tissue from the 3 dimensional imager, and in the event that the planned treatment position is not consonant with the effective patient plane of the 3 dimensional imager, obtain position information of the target tissue from the at least one 2 dimensional imager.

23 Claims, 3 Drawing Sheets

(51) Int. Cl.
*A61B 6/04* (2006.01)
*A61B 6/00* (2006.01)

(52) U.S. Cl.
CPC .......... *A61B 6/5235* (2013.01); *A61B 6/5247* (2013.01); *A61N 5/1049* (2013.01); *A61N 2005/1061* (2013.01)

(56) References Cited

U.S. PATENT DOCUMENTS 7,847,275 B2    12/2010  Lifshitz et al.
2008/0273659 A1*  11/2008  Guertin .................. A61B 6/032
                                                          378/65
2013/0229495 A1*  9/2013  Bani-Hashemi ......... A61B 6/00
                                                          348/47

OTHER PUBLICATIONS

Tadashi Kamada et al; "A horizontal CT system dedicated to heavy-ion beam treatment"; Radiotherapy and Oncology, Elsevier, Ireland, published Feb. 1, 1999, pp. 235-237.
International Search Report for PCT/IL2012/050149 mailed Aug. 30, 2012 by European Patent Office.
Written Opinion of the International Searching Authority for PCT/IL2012/050149 mailed Aug. 30, 2012 by European Patent Office.

* cited by examiner

UNIVERSAL TELETHERAPY TREATMENT ROOM ARRANGEMENT

CROSS-REFERENCE TO RELATED APPLICATIONS

This application claims priority from: U.S. Provisional Patent Application Ser. No. 61/481,205 filed May 1, 2011 entitled "Universal Teletherapy Treatment Room Arrangement", the entire contents of which are incorporated herein by reference.

TECHNICAL FIELD

The present disclosure relates generally to the field of teletherapy and in particular to a teletherapy treatment room arrangement comprising: a 3 dimensional imager; and a pair of 2 dimensional imagers arranged along planes orthogonal to the primary imaging plane of the 3 dimensional imager.

BACKGROUND OF THE INVENTION

Teletherapy is defined as a treatment methodology in which an irradiation source is at a distance from the body to be treated. X-rays and electron beams have long been used in teletherapy to treat various cancers. Unfortunately, X-rays exhibit a linear energy transfer approaching an exponential attenuation function, and are therefore of minimal safe use for deeply embedded growths. The use of heavy particles, particularly hadrons and more particularly protons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy. For clarity, this document will describe treatment as being accomplished with protons, however this is not meant to be limiting in any way.

The charged protons or ions can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

The above is accomplished in the prior art by a gantry system carrying a beam generating and delivery system. Unfortunately, the beam generating and delivery system is extremely heavy, and the need for such a gantry system leads to a prohibitively expensive structure limiting the number of available proton therapy centers. Such a gantry system does however advantageously treat the entire range of patients, irrespective of required irradiation angle.

An alternative to gantry systems is a fixed beam irradiation source, wherein irradiation is provided from a fixed location charged hadron source with optional post beam generation scanning or scattering functionality. In addition, fixed beam irradiation is not limited to that from a single treatment irradiation source, but can include multiple fixed beams which are independently controlled or jointly controlled. The term fixed beam is thus differentiated from a gantry system in that the treatment beam source is fixed in relation to the walls, floor and ceiling of the treatment room and is not generally movable.

It is to be noted that patient treatment for irradiation may be broadly broken into 2 groups: patients treated in a supine, prone and similar positions, also known as a horizontal treatment position; and patients treated in a seated or standing position, also known as a vertical treatment position. It is to be understood that the terms horizontal treatment and vertical treatment are not strictly limiting, and a range of angles about the strictly horizontal and the strictly vertical are included in each of the respective treatment positions. In particular, inclined treatment may be provided by either an inclination from the horizontal position or from the vertical position. Alternately, the beam may be inclined while the patient is in one of the horizontal and vertical positions.

Irradiation treatment is performed on a target tissue in a well defined process. In a first stage, known as the treatment planning stage, the target tissue is imaged and a treatment plan comprising dosage, patient position, and irradiation angles are defined. Furthermore, placement markers are defined, so as to ensure that subsequent irradiation sessions are properly targeted. Irradiation is then performed, responsive to the developed treatment plan, at a plurality of treatment sessions over a period of time, each session being known as a fraction. At each such fraction, care must be taken to ensure proper patient positioning, responsive to the placement markers, so as to avoid damage to organs in vicinity of the target tissue. Positioning of the patient responsive to the markers is performed based on visualization of the patient, responsive to the defined markers. Imaging performed with 3D imaging equipment, which according to the prior art is constituted of a CT scanner, advantageously may be used to both monitor the patient position compliant with the existing treatment plan and to determine validity of the existing treatment plan, since the CT scanner provides volumetric information to enable monitoring of anatomical changes within the target tissue. As a result, adjustment to the treatment plan may be performed responsive to the monitored anatomical changes within the target tissue.

U.S. Pat. No. 5,851,182 issued Dec. 22, 1998 to Sahadevan, the entire contents of which is incorporated herein by reference, is addressed to a patient setup and treatment verification system for radiation therapy having diagnostic imaging devices connected to a room containing a megavoltage radiation therapy machine. Daily patient setup for routine and three-dimensional conformal radiation therapy and on-line treatment port verification with superimposed isodose are done with a patient on a diagnostic imaging table. The patients are transferred from the diagnostic imaging table to the treatment table without changing the verified treatment position. Such a system is limited to a patient being treated in a supine position, thus requiring a costly gantry based irradiation system.

U.S. Pat. No. 7,847,275 issued Dec. 7, 2010 to Lifshitz et al., the entire contents of which is incorporated herein by reference, is addressed to a patient treatment arrangement comprising: a treatment irradiation source; and a patient positioning mechanism in communication with a patient support surface and operative to achieve positioning of the support surface equivalent to rotation of the patient support surface of at least 180° about any one of three orthogonal axes and translation of the patient support surface along any of three orthogonal axes. In addition an imager is provided arranged to image a target tissue at the irradiation angle. Such an imager adds cost to each treatment room, since commercially available imagers are primarily arranged to image patients in a fixed, predetermined position, generally horizontal.

U.S. Pat. No. 7,796,730 issued Sep. 14, 2010 to Marash et al., the entire contents of which is incorporated herein by reference, is addressed to an irradiation treatment apparatus comprising an imager arranged for vertical translation of a patient. Such an apparatus is ideal for vertical translation, however is not particularly appropriate for generally horizontal patient treatment positions.

There is thus a long felt need for an improved treatment arrangement which improves patient throughput by being usable for both horizontal treatment positions and vertical treatment positions.

SUMMARY OF THE INVENTION

Accordingly, it is a principal object of the present invention to overcome the disadvantages of prior art methods and arrangements of teletherapy. This is provided in the present invention by a teletherapy treatment arrangement comprising: a 3 dimensional imager exhibiting an effective patient plane and at least one 2 dimensional imager arranged to provide a pair of 2 dimensional images along planes generally orthogonal to the effective patient plane of the 3 dimensional imager. Preferably, the teletherapy treatment arrangement further provides a treatment irradiation source. The 3 dimensional imager may be provided with either a horizontal effective patient plane, or a vertical effective patient plane, and may be further adjustable to image over a range of angles in the general effective patient plane. In one embodiment the at least one 2 dimensional imager comprises a pair of 2 dimensional imagers arranged along the planes generally orthogonal to the effective patient plane of the 3 dimensional imager. In another embodiment a single 2 dimensional imager is provided in cooperation with a translation mechanism arranged to translate the single 2 dimensional imager alternately along planes orthogonal to the primary imaging plane of the 3 dimensional imager. Preferably, the at least one 2 dimensional imager is arranged to provide the pair of 2 dimensional imagers centered on the target tissue isocenter. Preferably, the 3 dimensional imager is arranged to provide 3 dimensional imaging centered on the target tissue isocenter and further preferably provides current volumetric information regarding the target tissue.

Positioning information for the patient, irrespective of treatment position, may thus be provided in any treatment room. In particular, in the event of a 3 dimensional imager arranged with a horizontal effective patient plane, a patient presenting a horizontal treatment position is positioned responsive to the 3 dimensional imager. Additionally, volumetric information of the target tissue is provided by the 3 dimensional imager. The one or more 2 dimensional imagers are preferably movable so as to enable free motion of the patient both in relation to the 3 dimensional imager and in relation to the irradiation source.

In the event of a 3 dimensional imager arranged with a horizontal effective patient plane, a patient presenting a vertical treatment position is positioned responsive to the at least one 2 dimensional imager providing a pair of 2 dimensional images along planes generally orthogonal to the primary imaging plane of the 3 dimensional image. Volumetric information of the target tissue is not provided at the current fraction.

In the event of a 3 dimensional imager arranged with a vertical effective patient plane, a patient presenting a vertical treatment position is positioned responsive to the 3 dimensional imager. Additionally, volumetric information of the target tissue is provided by the 3 dimensional imager. The one or more 2 dimensional imagers are preferably movable so as to enable free motion of the patient both in relation to the 3 dimensional imager and in relation to the irradiation source.

In the event of a 3 dimensional imager arranged with a vertical effective patient plane, a patient presenting a horizontal treatment position is positioned responsive to the at least one 2 dimensional imager providing a pair of 2 dimensional images along planes generally orthogonal to the primary imaging plane of the 3 dimensional image. Volumetric information of the target tissue is not provided at the current fraction.

In one embodiment the 2 dimensional imager comprises an x-ray panel in cooperation with an x-ray source. In another embodiment the 2 dimensional imager comprises a camera. In one further embodiment the camera is a stereo optic camera, thus providing 3 dimensional imaging without volumetric information regarding the target tissue, since penetrating rays are not utilized. Preferably, the at least one 2 dimensional imager and the 3 dimensional imager are provided in a single treatment room further arranged to provide a fixed beam irradiation treatment.

In one independent embodiment, a teletherapy treatment arrangement is provided, the provided teletherapy treatment arrangement comprising: a control unit; a 3 dimensional imager in communication with the control unit and responsive thereto, the 3 dimensional imager having an effective patient plane and arranged to image a patient target tissue; at least one 2 dimensional imager in communication with the control unit and responsive thereto, the at least one 2 dimensional imager arranged to provide a pair of 2 dimensional images along planes generally orthogonal to the effective patient plane of the 3 dimensional imager; and a patient positioner responsive to the control unit, the patient positioner arranged to secure a patient target tissue in a fixed spatial relationship to the patient positioner, the control unit arranged to: input a planned treatment position of the patient target tissue; in the event that the input planned treatment position is consonant with the effective patient plane of the 3 dimensional imager, obtain position information of the patient target tissue from the 3 dimensional imager; in the event that the input planned treatment position is not consonant with the effective patient plane of the 3 dimensional imager, obtain position information of the patient target tissue from the at least one 2 dimensional imager; and control the patient positioner so as to position the target tissue in relation to an irradiation source responsive to the obtained position information.

In one embodiment, in the event that the input planned treatment position is consonant with the effective patient plane of the 3 dimensional imager, the control unit is further arranged to obtain volumetric information of the patient target tissue from the 3 dimensional imager. In another embodiment, the obtained position information of the patient target tissue from the at least one 2 dimensional imager is responsive to the provided pair of 2 dimensional images.

In one embodiment, the teletherapy treatment arrangement further comprises: a set of walls defining a treatment room, wherein the 3 dimensional imager is at least partially within the defined treatment room; and wherein the at least one 2 dimensional imager is at least partially within the defined treatment room. In one further embodiment, the teletherapy treatment arrangement further comprises the irradiation source, wherein the irradiation source is a beam irradiation source fixed in relation to the set of walls.

In one embodiment, the at least one 2 dimensional imager comprises an x-ray panel in cooperation with an x-ray source. In another embodiment, the at least one 2 dimensional imager comprises a camera. In one further embodiment, the camera is a stereo optic camera.

In one embodiment, the effective patient plane of the 3 dimensional imager is horizontal. In another embodiment, the effective patient plane of the 3 dimensional imager is vertical.

In one embodiment, the at least one 2 dimensional imager comprises a pair of 2 dimensional imagers each arranged to provide a 2 dimensional image along a respective one of the planes generally orthogonal to the effective patient plane of the 3 dimensional imager. In another embodiment, the teletherapy treatment arrangement further comprises a translation mechanism, wherein the at least one 2 dimensional imager comprises a single 2 dimensional imager, the translation mechanism in communication with the single 2 dimensional imager and responsive to the control unit, the translation mechanism arranged to: translate the single 2 dimensional imager to a first position, the single 2 dimensional imager arranged to provide a 2 dimensional image along a first of the respective planes generally orthogonal to the effective patient plane of the provided 3 dimensional imager; and translate the single 2 dimensional imager to a second position, the single 2 dimensional imager arranged to provide a 2 dimensional image along a second of the respective planes generally orthogonal to the effective patient plane of the 3 dimensional imager.

In another independent embodiment, a teletherapy treatment room arrangement is provided, the teletherapy treatment room arrangement comprising: a set of walls defining a treatment room; a 3 dimensional imager at least partially within the defined treatment room, the 3 dimensional imager having an effective patient plane and arranged to image a patient target tissue; and at least one 2 dimensional imager within the defined treatment room and arranged to provide a pair of 2 dimensional images along planes generally orthogonal to the effective patient plane of the 3 dimensional imager.

In one embodiment, the teletherapy treatment room arrangement further comprises: a control unit in communication with each of the 3 dimensional imager and the at least one 2 dimensional imager, each of the 3 dimensional imager and the at least one 2 dimensional imager responsive to the control unit; and a patient positioner responsive to the control unit, the control unit arranged to: input a planned treatment position of a patient target tissue disposed in a fixed spatial relationship to the patient positioner; in the event that the input planned treatment position is consonant with the effective patient plane of the 3 dimensional imager, obtain position information of the patient target tissue from the 3 dimensional imager; in the event that the input planned treatment position is not consonant with the effective patient plane of the 3 dimensional imager, obtain position information of the patient target tissue from the at least one 2 dimensional imager; and control the patient positioner so as to position the target tissue in relation to an irradiation source responsive to the obtained position information. In one further embodiment, in the event that the input planned treatment position is consonant with the effective patient plane of the 3 dimensional imager, the control unit is further arranged to obtain volumetric information of the patient target tissue from the 3 dimensional imager.

In one independent embodiment, a method of teletherapy treatment is provided, the method comprising: providing a 3 dimensional imager having an effective patient plane and arranged to image a patient target tissue; providing at least one 2 dimensional imager arranged to provide a pair of 2 dimensional images along planes generally orthogonal to the effective patient plane of the provided 3 dimensional imager; inputting a planned treatment position of a patient target tissue; in the event that the input planned treatment position is consonant with the effective patient plane of the provided 3 dimensional imager, obtaining position information of the patient target tissue from the provided 3 dimensional imager, and in the event that the input planned treatment position is not consonant with the effective patient plane of the provided 3 dimensional imager, obtaining position information of the patient target tissue from the at least one 2 dimensional imager by providing the pair of 2 dimensional images; and positioning the target tissue in relation to an irradiation source responsive to the obtained position information.

In one embodiment, the method further comprises: in the event that the input planned treatment position is consonant with the effective patient plane of the provided 3 dimensional imager, obtaining volumetric information for the patient target tissue from the provided 3 dimensional imager. In another embodiment the provided at least one 2 dimensional imager comprises an x-ray panel in cooperation with an x-ray source.

In one embodiment, the provided at least one 2 dimensional imager comprises a camera. In one further embodiment, the camera comprises a stereo optic camera.

In one embodiment, the effective patient plane of the provided 3 dimensional imager is horizontal. In another embodiment, the effective patient plane of the provided 3 dimensional imager is vertical.

In one embodiment, the provided at least one 2 dimensional imager comprises a pair of 2 dimensional imagers each arranged to provide a 2 dimensional image along a respective one of the planes generally orthogonal to the effective patient plane of the provided 3 dimensional imager. In another embodiment, the provided at least one 2 dimensional imager comprises a single 2 dimensional imager, the method further comprising: translating the single 2 dimensional imager to a first position orthogonal to the effective patient plane of the provided 3 dimensional imager; imaging a first of the pair of 2 dimensional images in the first position; translating the single 2 dimensional imager to a second position orthogonal to the first position and orthogonal to the effective patient plane of the provided 3 dimensional imager; and imaging a second of the pair of 2 dimensional images in the second position.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1A:
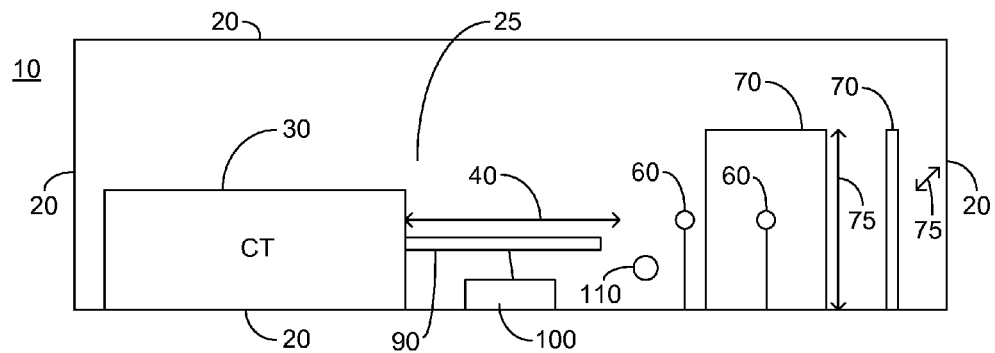
FIG. 1A illustrates a high level side view of an exemplary embodiment of a teletherapy treatment arrangement exhibiting a 3 dimensional imager with a horizontal effective patient plane, and a pair of 2 dimensional imagers.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1B:
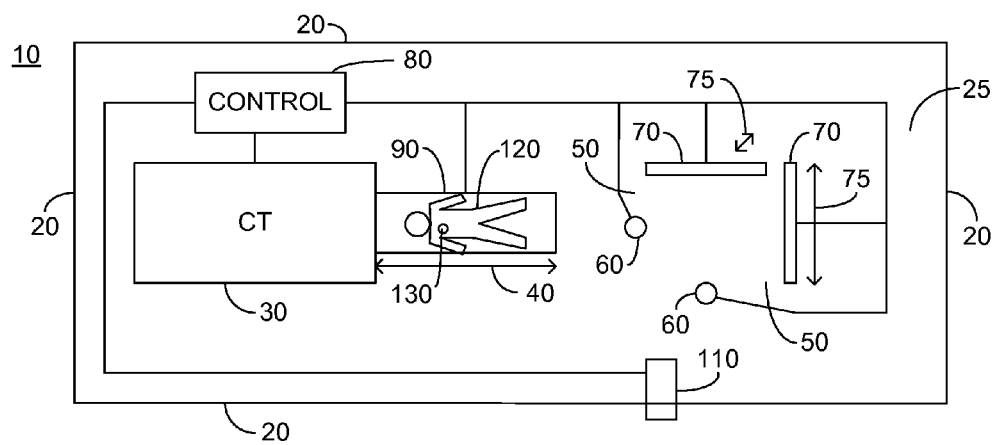
FIG. 1B illustrates a high level top view of the teletherapy treatment arrangement of FIG. 1A.

FIG. 1A illustrates a high level side view of an exemplary embodiment of a teletherapy treatment arrangement 10 and FIG. 1B illustrates a high level top view of teletherapy treatment arrangement 10, the description of FIGS. 1A and 1B being taken together. Teletherapy treatment arrangement 10 comprises: a plurality of generally linear surfaces 20 defining a treatment room 25, with generally linear surfaces 20 comprising walls, floor and a ceiling; a 3 dimensional imager 30 having a effective patient plane 40; a pair of 2 dimensional imagers 50, each comprising an imaging source 60 and an imaging panel 70 arranged along a plane 75; a control unit 80; a patient platform 90; a patient positioner 100; and a treatment irradiation source 110. A patient 120 exhibiting a target tissue 130 is further illustrated, patient 120 secured to patient platform 90.

In one embodiment, treatment irradiation source 110 is a fixed beam irradiation source. In one embodiment, 3 dimensional imager 30 comprises a computerized tomography (CT) imager, or other 3 dimensional imager arranged to provide current volumetric information regarding the target tissue. In one embodiment, each imaging source 60 is arranged to output x-rays. In another embodiment (not shown), each 2 dimensional imager 50 comprises a camera in place of imaging source 60 and no imaging panel 70 is necessary. In one further embodiment each camera instance of 2 dimensional imager 50 comprises a stereo-optic camera, thus further providing depth information, without providing current volumetric information regarding the target tissue, since penetrating rays are not provided by the camera equipment. 3 dimensional imager 30 is illustrated as being within treatment room 25, however this is not meant to be limiting in any way. In one embodiment, 3 dimensional imager 30 is only partially within treatment room 25. In another embodiment, 3 dimensional imager 30 and 2 dimensional imagers 50 are situated within separate rooms. Effective patient plane 40 is horizontal. Patient platform 90 is illustrated in a horizontal position, however this is not meant to be limiting in any way and, as will be further described, patient platform 90 can be in a vertical position. As described above, the terms horizontal and vertical are not strictly limiting and a range of angles is specifically contemplated. Plane 75 of each imaging panel 70 is generally orthogonal to effective patient plane 40 of 3 dimensional imager 30. In one embodiment, both planes 75 are generally orthogonal to each other.

Control unit 80 is in communication with 3 dimensional imager 30, each imaging source 60, each imaging panel 70, patient positioner 100 and treatment irradiation source 110. Patient positioner 100 is in communication with patient platform 90 and is arranged to articulate patient platform 90 to the desired positioning.

In operation, control unit 80 is arranged to input a planned treatment position of target tissue 130, i.e. one of a horizontal and vertical position of patient platform 90. In one embodiment, the planned treatment position is determined responsive to data stored on a memory of control unit 80, preferably further responsive to a user input, such as a user ID. In another embodiment, the planned treatment position is determined responsive to a user input. In another embodiment, the planned treatment position is determined responsive to information received from an external server.

In the event that the input planned treatment position of target tissue 130 is consonant with effective patient plane 40, i.e. the input planned position of patient platform 90 is horizontal, position information of target tissue 130 is obtained from 3 dimensional imager 30. Specifically, control unit 80 is arranged to control patient positioner 100 to position patient platform 90 such that target tissue 130 is within 3 dimensional imager 30 and is further arranged to control 3 dimensional imager 30 to image patient 120, specifically target tissue 130. In one embodiment, the position information of target tissue 130 comprises the position of target tissue 130, specifically the isocenter of target tissue 130, in relation to patient positioner 100. In another embodiment position information is provided responsive to predetermined markers, which may be expressed as specific skeletal structures. In one embodiment, volumetric information of target tissue 130 is further obtained from 3 dimensional imager 30. Volumetric information provides for both: patient positioning according to the existing treatment plan based on visualization of the target tissue; and assessment of the plan validity given visualized changes of target tissue 130. Qualified personnel may adapt the treatment plan responsive to the visualized changes of target tissue 130, and record the adaptation for future fractions, in addition to utilizing the adaptation for the current fraction.

Control unit 80 is further arranged to translate patient positioner 100 such that target tissue 130 is in a position to be irradiated by treatment irradiation source 110 in accordance with the input planned treatment position of target tissue 130, optionally modified responsive to the obtained volumetric information. Preferably, the positioning of target tissue 130 is arranged such that the isocenter of target tissue 130 is positioned to be maximally irradiated by treatment irradiation source 110. Control unit 80 is further arranged to control treatment irradiation source 110 to irradiate target tissue 130 in accordance with the treatment plan, as optionally adapted.

In the event that the input planned treatment position of target tissue 130 is not consonant with effective patient plane 40, i.e. the input planned position of patient platform 90 is vertical, position information of target tissue 130 is obtained from 2 dimensional imagers 50. Specifically, control unit 80 is arranged to control patient positioner 100 to position patient platform 90 such that target tissue 130, or another marker, is positioned between imaging source 60 and imaging panel 70 of each 2 dimensional imager 50. Control unit 80 is further arranged to control each 2 dimensional imager 50 to image patient 120, specifically one or more of target tissue 130 and at least one pre-determined marker. In one embodiment, each 2 dimensional imager 50 is controlled to image at different times so that the radiation output from image sources 60 don't interfere with each other. In one embodiment, the position information of target tissue 130 comprises the position of target tissue 130, specifically the isocenter of target tissue 130, in relation to patient platform 90. In an embodiment where each 2 dimensional imager 50 comprises a camera, control unit 80 is arranged to control patient positioner 100 to position patient platform 90 such that patient 120, specifically target tissue 130, is positioned in front of both 2 dimensional imagers 50. Pre-determined markers, such as skeletal features, are utilized by control unit 80 to determine the precise position of target tissue 130. Volumetric changes to target tissue 130 are not visualized. Each 2 dimensional imager 50 may comprise a plurality of 2 dimensional imagers to provide 3 dimensional imaging, such as a stereo-optic camera image, however typically current volumetric information of target tissue 130 is not provided.

Control unit 80 is further arranged to control each 2 dimensional imager 50 to image patient 120. In one embodiment, the position information of target tissue 130 comprises the position of target tissue 130, specifically the isocenter of target tissue 130, in relation to patient positioner 100, determined in relation to at least one predetermined maker, such as a skeletal feature. In the embodiment where each 2 dimensional imager 50 comprises a camera, the position information of target tissue 130 comprises the position of patient 120 in relation to patient positioner 100. Responsive to the combination of the obtained position information of patient 120 with prior information regarding the location of target tissue 130 within patient 120, the position of target tissue 130 is determined. In one embodiment, the determined information regarding the location of target tissue 130 within patient 120 is stored on a memory of control unit 80.

As will be described below in relation to FIGS. 2A and 2B, a single 2 dimensional imager may be provided with a translation mechanism, the translation mechanism arranged to translate the single 2 dimensional imager along each plane 75, an image being provided at each position of the single 2 dimensional imager. The translation mechanism may be arranged to provide multiple degrees of motion along any of a plurality of axes and planes without exceeding the scope.

In one embodiment, treatment irradiation source 110 is positioned such that in the event that patient 120 is imaged by pair of 2 dimensional imagers 50, no further translation of patient positioner 100 is required for target tissue 130 to be irradiated by treatment irradiation source 110.

Control unit 80 is further arranged to translate patient positioner 100 such that target tissue 130 is in a position to be irradiated by treatment irradiation source 110 in accordance with input planned treatment position of target tissue 130, optionally modified responsive to the obtained volumetric information. Preferably, the positioning of target tissue 130 is arranged such that the isocenter of target tissue 130 is positioned to be maximally irradiated by treatment irradiation source 110. Control unit 80 is further arranged to control treatment irradiation source 110 to irradiate target tissue 130 according to the treatment plan. Such an arrangement provides for irradiation of target tissue 130 at each fraction, irrespective of room availability, i.e. a patient with a treatment plan not consonant with the imaging plane of a 3 dimensional imager may still be treated in the treatment room with the non-consonant 3 dimensional imager, responsive to the 2 dimensional imagers 50. Typically, no treatment plan adaption is performed at such a fraction, since volumetric information of target tissue 130 is not provided.

Figure 2A:
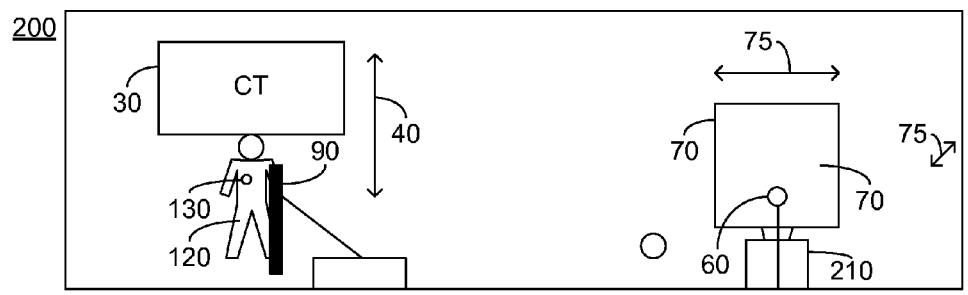
FIG. 2A illustrates a high level side view of an exemplary embodiment of a teletherapy treatment arrangement exhibiting a 3 dimensional imager, with a vertical effective patient plane, and a single 2 dimensional imager.
Figure 2B:
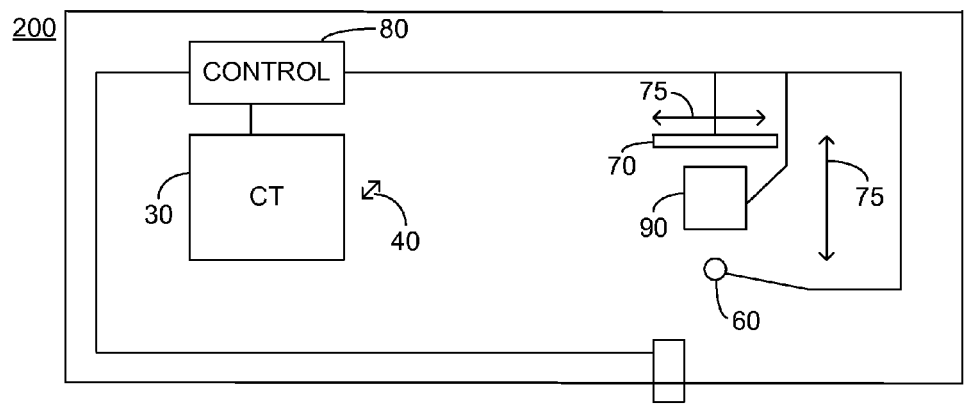
FIG. 2B illustrates a high level top view of the teletherapy treatment arrangement of FIG. 2A.

FIG. 2A illustrates a high level side view of an exemplary embodiment of a teletherapy treatment arrangement 200. Teletherapy treatment arrangement 200 is in all respects similar to teletherapy treatment arrangement 10, with the exception that effective patient plane 40 of 3 dimensional imager 30 is vertical and only a single 2 dimensional imager 50 is provided along a first of the orthogonal planes 75. Additionally, teletherapy treatment arrangement 200 further comprises a translation mechanism 210 connected to 2 dimensional imager 50 and in communication with control unit 80. FIG. 2B illustrates a high level top view of teletherapy treatment arrangement 200 with patient platform 90 situated between imaging source 60 and imaging panel 70 of 2 dimensional imager 50, the description of FIGS. 2A and 2B being taken together.

The operation of teletherapy treatment arrangement 200 is in all respects similar to the operation of teletherapy treatment arrangement 10, with the exception that the planned treatment position of target tissue 130 is consonant with effective patient plane 40 of 3 dimensional imager 30 when the planned treatment position is vertical. Additionally, in the event that the planned treatment position of target tissue 130 is not consonant with effective patient plane 40 of 3 dimensional imager 30, i.e. the planned treatment position is horizontal, patient 120, specifically target tissue 130, is imaged by single 2 dimensional imager 50. As described above in relation to teletherapy treatment arrangement 10, target tissue 130 is imaged along both planes 75 generally orthogonal to effective treatment plane 40. After target tissue 130 is imaged by 2 dimensional imager 50 along the first plane 75, control unit 80 is arranged to control translation mechanism 210 to translate 2 dimensional imager 50 so as to provide an image along the second plane 75.

In one embodiment, translation mechanism 210 is in communication with both imaging source 60 and imaging panel 70 of 2 dimensional imager 50 and is arranged to translate imaging panel 70 to be along the second plane 75 and to translate imaging source 60 to be opposing imaging panel 70 so as to allow imaging of target tissue 130 along the second plane 75. In one embodiment, translation mechanism 210 is arranged such that there is no need to further translate or adjust the position of patient platform 90 in order to image target tissue 130 when imaging panel 70 is along the second plane 75. In one non-limiting embodiment, translation mechanism 210 is situated within a rail and is translated along the rail to accomplish the translation of 2 dimensional imager 50. There is no requirement that translation mechanism 210 be restricted to translation along a predetermined plane, and translation mechanism 210 may be arranged to provide motion along a plurality of planes and axes without limitation. In the embodiment where 2 dimensional imager 50 comprises a camera, translation mechanism 210 is arranged to translate the camera to the proper position for imaging along the second plane 75, similar to the translation of imaging source 60. Control unit 80 controls 2 dimensional imager 50 to image target tissue 130 along the second plane 75 and target tissue 130 is treated as described above. In one embodiment, 2 dimensional imager 50 comprises a plurality of 2 dimensional imagers, such as a stereo optic camera, thus providing 3 dimensional capabilities typically without providing volumetric information of target tissue 130.

Teletherapy treatment arrangement 200 has been described in an embodiment wherein only a single 2 dimensional imager 50 is provided, however this is not meant to be limiting in any. In another embodiment, treatment arrangement 200 comprises a pair of 2 dimensional imagers, as described above in relation to treatment arrangement 10 of FIGS. 1A and 1B. Each of the 2 dimensional imagers 50 may comprise a plurality of 2 dimensional imagers, forming in one particular embodiment a stereo optic camera, thus providing 3 dimensional capabilities typically without providing volumetric information of target tissue 130.

Figure 3:
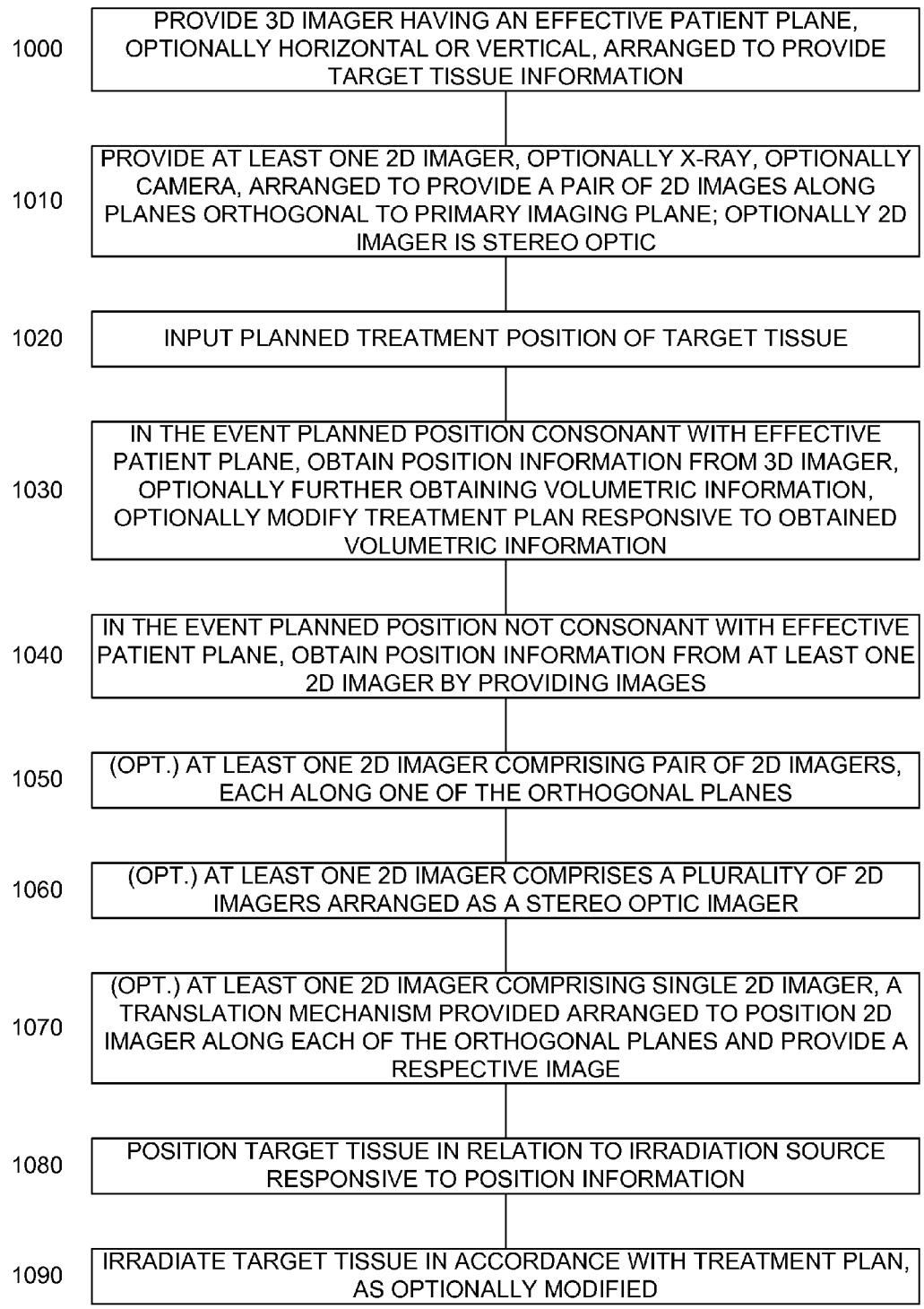
FIG. 3 illustrates a high level flow chart of an exemplary method of teletherapy treatment.

FIG. 3 illustrates a high level flow chart of a method of teletherapy treatment according to certain embodiments. In stage 1000, a 3 dimensional imager is provided, having an effective patient plane and arranged to provide current volumetric information for a target tissue. In one embodiment, the effective patient plane is horizontal. In another embodiment, the effective patient plane is vertical. In one embodiment, the provided 3 dimensional imager comprises a CT imager. In stage 1010, at least one 2 dimensional imager is provided, the at least one 2 dimensional imager arranged to provide a pair of 2 dimensional images each along a plane generally orthogonal to the effective patient plane of the 3 dimensional imager of stage 1000. In one embodiment, the at least one 2 dimensional imager comprises at least one x-ray imager. In another embodiment, the at least one 2 dimensional imager comprises at least one camera. In another embodiment the at least one 2 dimensional imager comprises a plurality of 2 dimensional imagers arranged to provide 3 dimensional information, such as a stereo optic camera. The at least one 3 dimensional imager typically does not provide current volumetric information for the target tissue.

In stage 1020, a planned treatment position of a target tissue of a patient is input. In one embodiment, the planned treatment position is one of horizontal and vertical. In stage 1030, in the event the planned treatment position of stage 1020 is consonant with the effective patient plane of the provided 3 dimensional imager of stage 1000, position information of the target tissue is obtained from the provided 3 dimensional imager. In one embodiment, the position information comprises the position of the isocenter of the target tissue in relation to a patient positioner in physical communication with a patient platform having the patient secured thereto. Position information may be provided responsive to one or more markers of the patient, or responsive to volumetric information of the target tissue. Optionally the markers comprise patient skeletal features or fiducial markers. Optionally, the obtained volumetric information may be utilized for treatment planning adaptation.

In stage 1040, in the event the planned treatment position is not consonant with the effective patient plane of the provided 3 dimensional imager of stage 1000, position information of the target tissue is obtained from the at least one 2 dimensional imager. Specifically the at least one 2 dimensional imager is arranged to provide a pair of 2 dimensional images each along a respective plane generally orthogonal to the effective patient plane of the provided 3 dimensional imager of stage 1000, the position information determined responsive to the provided 2 dimensional images. In one embodiment, the position information comprises the position of the isocenter of the target tissue in relation to a patient platform having the patient secured thereto. Position information may be derived from markers, such as skeletal features, without exceeding the scope.

In optional stage 1050, the provided at least one 2 dimensional imager of stage 1010 comprises a pair of 2 dimensional imagers each arranged to provide a 2 dimensional image along one of the planes generally orthogonal to the effective patient plane of the provided 3 dimensional imager of stage 1000. In one embodiment, a first of the pair of 2 dimensional imagers is arranged to provide a 2 dimensional image along a first plane and the second of the pair of 2 dimensional imagers is arranged to provide a 2 dimensional image along a second plane, the first plane generally orthogonal to the second plane. In optional stage 1060, the provided at least one 2 dimensional imager of stage 1010 comprises a plurality 2 dimensional imagers arranged as a stereo optic camera. In optional stage 1070, the provided at least one 2 dimensional imager of stage 1010 comprises a single 2 dimensional imager and a translation mechanism in communication with the single 2 dimensional imager is further provided. The provided translation mechanism is arranged to translate the single 2 dimensional imager such that the single 2 dimensional imager provides a 2 dimensional image along each of the planes generally orthogonal to the effective patient plane of the provided 3 dimensional imager of stage 1000.

In stage 1080, the target tissue is positioned in relation to an irradiation source responsive to the obtained position information of either stage 1030 or 1040, either according to the original treatment, or according to an adapted treatment plan, as described above in relation to stage 1030. In one embodiment, positioning the target tissue comprises positioning the patient platform, having the patient secured thereto, in relation to an irradiation source such that the isocenter of the target tissue is in position to receive a treatment beam from the irradiation source. Preferably the irradiation source is a fixed beam irradiation source.

In stage 1090, irradiation of target tissue from the preferably fixed beam irradiation source is performed in accordance with the treatment plan, as optionally adapted as described above in relation to stage 1030.

With such arrangements as described above, any patient can be treated in any treatment room. Thus, a treatment center provided with either a teletherapy treatment arrangement 10, as described above in relation to FIGS. 1A-1B, or a teletherapy treatment arrangement 200, as described above in relation to FIGS. 2A-2B is advantageously able to provide improve patient throughput, since patients are not confined to a treatment room having a 3 dimensional imager with an effective patient plane consonant with the required treatment position of the patient.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. A teletherapy treatment arrangement comprising:
   a control unit;
   a 3 dimensional imager in communication with said control unit and responsive thereto, said 3 dimensional imager having an effective patient plane and arranged to image a patient target tissue;
   at least one 2 dimensional imager in communication with said control unit and responsive thereto, said at least one 2 dimensional imager arranged to provide a pair of 2dimensional images along planes generally orthogonal to the effective patient plane of said 3 dimensional imager; and
   a patient positioner responsive to said control unit, said patient positioner arranged to secure a patient target tissue in a fixed spatial relationship to said patient positioner,
   said control unit arranged to:
      input a planned treatment position of the patient target tissue;
      in the event that said input planned treatment position is consonant with the effective patient plane of said 3 dimensional imager, obtain position information of the patient target tissue from said 3 dimensional imager;
      in the event that said input planned treatment position is not consonant with the effective patient plane of said 3 dimensional imager, obtain position information of the patient target tissue from said at least one 2 dimensional imager; and
      control said patient positioner so as to position the target tissue in relation to an irradiation source responsive to said obtained position information.

2. The teletherapy treatment arrangement according to claim 1, wherein in the event that said input planned treatment position is consonant with the effective patient plane of said 3 dimensional imager, said control unit is further arranged to obtain volumetric information of the patient target tissue from said 3 dimensional imager.

3. The teletherapy treatment arrangement according to claim 1, wherein said obtained position information of the patient target tissue from said at least one 2dimensional imager is responsive to the provided pair of 2 dimensional images.

4. The teletherapy treatment arrangement according to claim 1, further comprising:
   a set of walls defining a treatment room,
   wherein said 3 dimensional imager is at least partially within said defined treatment room; and
   wherein said at least one 2 dimensional imager is at least partially within said defined treatment room.

5. The teletherapy treatment arrangement according to claim 4, further comprising the irradiation source, wherein said irradiation source is a beam irradiation source fixed in relation to said set of walls.

6. The teletherapy treatment arrangement according to claim 1, wherein said at least one 2 dimensional imager comprises an x-ray panel in cooperation with an x-ray source.

7. The teletherapy treatment arrangement according to claim 1, wherein said at least one 2 dimensional imager comprises a camera.

8. The teletherapy treatment arrangement according to claim 7, wherein the camera is a stereo optic camera.

9. The teletherapy treatment arrangement according to claim 1, wherein the effective patient plane of said 3 dimensional imager is horizontal.

10. The teletherapy treatment arrangement according to claim 1, wherein the effective patient plane of said 3 dimensional imager is vertical.

11. The teletherapy treatment arrangement according to claim 1, wherein said at least one 2 dimensional imager comprises a pair of 2 dimensional imagers each arranged to provide a 2 dimensional image along a respective one of the planes generally orthogonal to the effective patient plane of said 3 dimensional imager.

12. The teletherapy treatment arrangement according to claim 1, further comprising a translation mechanism, wherein said at least one 2 dimensional imager comprises a single 2 dimensional imager, said translation mechanism in communication with said single 2 dimensional imager and responsive to said control unit, said translation mechanism arranged to:
   translate said single 2 dimensional imager to a first position, said single 2dimensional imager arranged to provide a 2 dimensional image along a first of the respective planes generally orthogonal to the effective patient plane of said provided 3 dimensional imager; and
   translate said single 2 dimensional imager to a second position, said single 2 dimensional imager arranged to provide a 2 dimensional image along a second of the respective planes generally orthogonal to the effective patient plane of said 3 dimensional imager.

13. A teletherapy treatment room arrangement comprising:
   a set of walls defining a treatment room;
   a 3 dimensional imager at least partially within said defined treatment room, said 3dimensional imager having an effective patient plane and arranged to image a patient target tissue:
   at least one 2 dimensional imager within said defined treatment room and arranged to provide a pair of 2 dimensional images along planes generally orthogonal to the effective patient plane of said 3 dimensional imager;
   a control unit in communication with each of said 3 dimensional imager and said at least one 2 dimensional imager, each of said 3 dimensional imager and said at least one 2dimensional imager responsive to said control unit; and a patient positioner responsive to said control unit,
said control unit arranged to:
  input a planned treatment position of a patient target tissue disposed in a fixed spatial relationship to said patient positioner;
  in the event that said input planned treatment position is consonant with the effective patient plane of said 3 dimensional imager, obtain position information of the patient target tissue from said 3 dimensional imager;
  in the event that said input planned treatment position is not consonant with the effective patient plane of said 3 dimensional imager, obtain position information of the patient target tissue from said at least one 2 dimensional imager; and
  control said patient positioner so as to position the target tissue in relation to an irradiation source responsive to said obtained position information.

14. The teletherapy treatment room arrangement according to claim 13, wherein in the event that said input planned treatment position is consonant with the effective patient plane of said 3 dimensional imager, said control unit is further arranged to obtain volumetric information of the patient target tissue from said 3 dimensional imager.

15. A method of teletherapy treatment comprising:
  providing a 3 dimensional imager having an effective patient plane and arranged to image a patient target tissue;
  providing at least one 2 dimensional imager arranged to provide a pair of 2dimensional images along planes generally orthogonal to the effective patient plane of said provided 3 dimensional imager;
  inputting a planned treatment position of a patient target tissue;
    in the event that said input planned treatment position is consonant with the effective patient plane of said provided 3 dimensional imager, obtaining position information of the patient target tissue from said provided 3 dimensional imager, and
    in the event that said input planned treatment position is not consonant with the effective patient plane of said provided 3 dimensional imager, obtaining position information of the patient target tissue from said at least one 2 dimensional imager by providing the pair of 2 dimensional images; and
  positioning the target tissue in relation to an irradiation source responsive to said obtained position information.

16. The method according to claim 15, further comprising:
  in the event that said input planned treatment position is consonant with the effective patient plane of said provided 3 dimensional imager, obtaining volumetric information for the patient target tissue from said provided 3 dimensional imager.

17. The method according to claim 15, wherein said provided at least one 2dimensional imager comprises an x-ray panel in cooperation with an x-ray source.

18. The method according to claim 15, wherein said provided at least one 2dimensional imager comprises a camera.

19. The method according to claim 18, wherein the camera comprises a stereo optic camera.

20. The method according to claim 15, wherein the effective patient plane of said provided 3 dimensional imager is horizontal.

21. The method according to claim 15, wherein the effective patient plane of said provided 3 dimensional imager is vertical.

22. The method according to claim 15, wherein said provided at least one 2 dimensional imager comprises a pair of 2 dimensional imagers each arranged to provide a 2 dimensional image along a respective one of the planes generally orthogonal to the effective patient plane of said provided 3 dimensional imager.

23. The method according to claim 15, wherein said provided at least one 2 dimensional imager comprises a single 2 dimensional imager, the method further comprising:
  translating said single 2 dimensional imager to a first position orthogonal to said effective patient plane of said provided 3 dimensional imager;
  imaging a first of the pair of 2 dimensional images in said first position;
  translating said single 2 dimensional imager to a second position orthogonal to said first position and orthogonal to said effective patient plane of said provided 3 dimensional imager; and
  imaging a second of the pair of 2 dimensional images in said second position.

* * * * *